(12) United States Patent
Melsheimer

(10) Patent No.: US 8,449,494 B2
(45) Date of Patent: May 28, 2013

(54) APPARATUS AND METHOD FOR PREPARING FOAM

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 547 days.

(21) Appl. No.: 12/639,379

(22) Filed: Dec. 16, 2009

(65) Prior Publication Data

US 2011/0144568 A1   Jun. 16, 2011

(51) Int. Cl.
*A61M 37/00* (2006.01)

(52) U.S. Cl.
USPC ............ 604/24; 604/23; 604/83; 604/85; 604/191; 604/218; 604/82; 604/506

(58) Field of Classification Search
USPC ............ 604/83, 85, 23–24, 506, 82, 218, 604/191
See application file for complete search history.

(56) References Cited

U.S. PATENT DOCUMENTS

| | | | |
|---|---|---|---|
| 857,739 A | 6/1907 | Kennerly et al. | |
| 2,074,401 A | 3/1937 | Kauzal | |
| 3,721,244 A | 3/1973 | Elmaleh | |
| 3,754,687 A * | 8/1973 | Norton | 73/864.14 |
| 4,044,758 A | 8/1977 | Patel | |
| 4,654,027 A | 3/1987 | Dragan et al. | |
| 5,127,552 A | 7/1992 | Bauman et al. | |
| 5,304,147 A | 4/1994 | Johnson et al. | |
| 5,658,248 A | 8/1997 | Klein | |
| 6,059,759 A | 5/2000 | Mottola et al. | |
| 7,484,642 B2 | 2/2009 | Bonney | |
| 2002/0077589 A1 | 6/2002 | Tessari | |
| 2006/0161113 A1 | 7/2006 | Denolly | |
| 2006/0178620 A1 | 8/2006 | Wollmann et al. | |
| 2007/0088252 A1* | 4/2007 | Pestotnik et al. | 604/82 |
| 2007/0112308 A1 | 5/2007 | Kay et al. | |
| 2008/0114295 A1 | 5/2008 | Glynn | |
| 2008/0145401 A1 | 6/2008 | Osman et al. | |
| 2009/0247985 A1 | 10/2009 | Melsheimer et al. | |

* cited by examiner

Primary Examiner — Kevin C Sirmons
Assistant Examiner — Edelmira Bosques
(74) *Attorney, Agent, or Firm* — Brinks Hofer Gilson & Lione

(57) ABSTRACT

A device and a method for preparing foam are provided. The device includes a first housing having a first chamber therein and a first movable member positioned at least partially within the first housing. The device also includes a second housing having a second chamber therein, the second chamber being selectively and operably connectable to the first chamber. The second housing further includes a biasing member and a second movable member therein, the biasing member biasing the movable member toward a first end portion of the second housing. The device includes a valve operably connected to the first chamber and the second chamber and movably positionable to selectively control the connection between the first chamber and the second chamber and a handle operably connected to the first movable member and movable to bias the first movable member toward a first end portion of the first housing.

19 Claims, 7 Drawing Sheets

APPARATUS AND METHOD FOR PREPARING FOAM

TECHNICAL FIELD

This invention generally relates to medical devices and in particular to an apparatus and method for preparing foam for injection into a patient during a medical procedure.

BACKGROUND

Minimally invasive medical procedures are performed in various vessels and ducts in the body. In some procedures, it is desirable to treat varicose veins using minimally invasive procedures.

One minimally invasive procedure for treating varicose veins, for example, includes the endovascular injection of a sclerosing agent to ablate the diseased veins. Preferably the sclerosing agent is provided in the form of foam having greater viscosity than a liquid sclerosing agent.

A foam is prepared by agitating the liquid scleroscent with air or other type of gas to create the foam. Typically, two individual syringes connected together through Luer connections with a stopcock and the two syringes are used to prepare the foam. One syringe is used to introduce the liquid sclerosing agent to the system while the other syringe is used to introduce the gas. The operator then utilizes both hands to alternatively depress the syringe plungers, rapidly forcing the sclerosing agent and air mixture through the narrowed ends of the syringes to produce foam for injection into a patient.

Problems may arise with the use of two individual syringes however. The Luer connections with the syringes and the stopcock may leak if the proper mating of the Luer connectors is not made to the stopcock or the torquing of the connection is not proper to create a seal. In addition, the dual syringes require that the operator use both hands to generate the foam and thus, prevents the operator from any other operations at the same time. Further the amount of pressure necessary to depress the plungers of the syringes to repeatedly exchange the sclerosing agent to generate the foam may be very high and difficult to repeat a sufficient number of times to generate foam sufficiently viscous to inject into the patient.

There is a need for a device and a method to provide a leak-free system to generate foam for injection into a patient and that can provide single-handled operation and avoid operator fatigue.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a device for preparing foam. The device includes a first housing having a first chamber therein and a first movable member positioned at least partially within the first housing. The device also includes a second housing having a second chamber therein, the second chamber being selectively and operably connectable to the first chamber. The second housing further includes a biasing member and a second movable member therein, the biasing member biasing the movable member toward a first end portion of the second housing. The device includes a valve operably connected to the first chamber and the second chamber and movably positionable to selectively control the connection between the first chamber and the second chamber and a handle operably connected to the first movable member and movable to bias the first movable member toward a first end portion of the first housing.

In another aspect of the present invention, a method for implanting a preparing and delivering foam is provided. The method includes providing a device for preparing foam. The device includes a first housing having a first chamber therein and a first movable member positioned at least partially within the first housing. The device also includes a second housing having a second chamber therein, the second chamber being selectively and operably connectable to the first chamber. The second housing also including a biasing member and a second movable member therein, the biasing member biasing the movable member toward a first end portion of the second housing. The device includes a valve operably connected to the first chamber and the second chamber and movably positionable to selectively control the connection between the first chamber and the second chamber and a handle operably connected to the first movable member. The method further includes depressing a portion of the handle to move the handle from a first position to a second position and biasing the first movable member toward a first end portion of the first housing to force a liquid out of the first chamber and into the second chamber and compressing the biasing member toward a second end portion of the first housing as the liquid is forced into the second chamber. The method includes expanding the biasing member toward the first end portion of the second housing to move the second movable member toward the first end portion of the second housing to force the liquid from the second chamber into the first chamber and moving the first movable member and handle back to the first position.

DETAILED DESCRIPTION OF THE EMBODIMENTS

Figure 1:
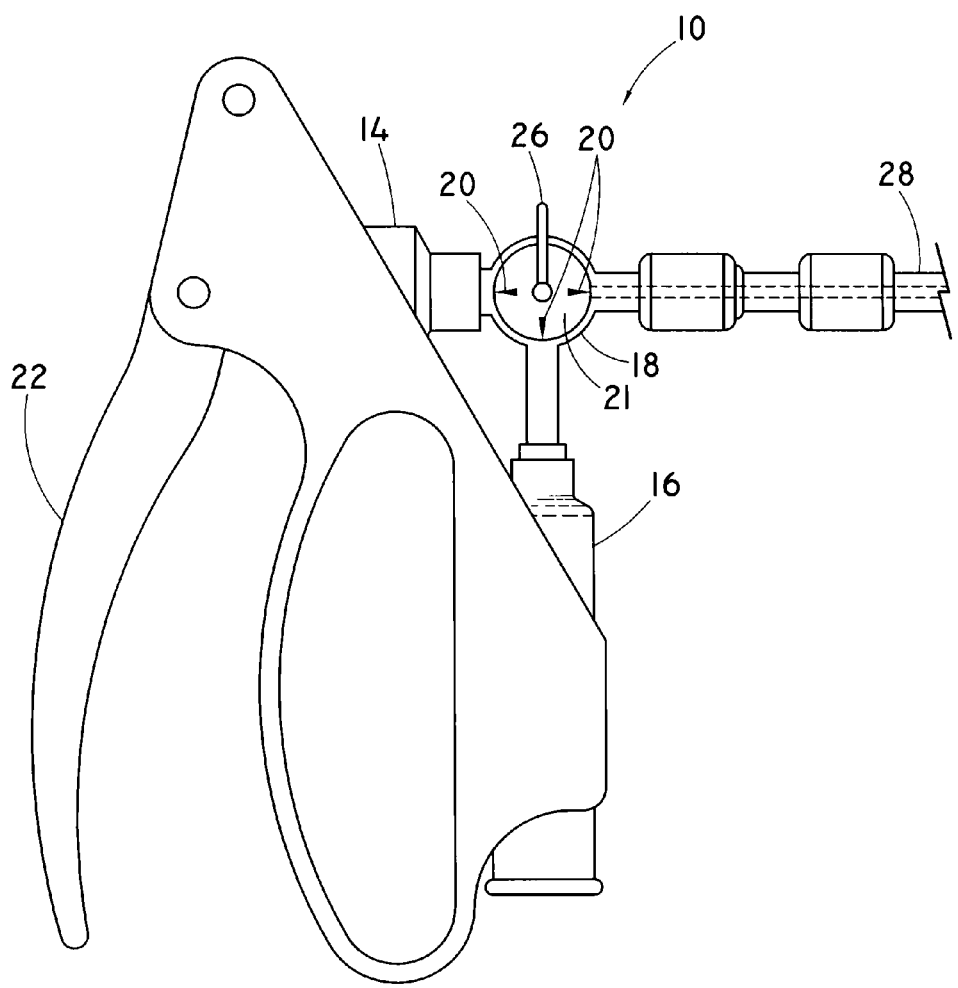
FIG. 1 is a side view of a device according to an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the foam to a patient. Hence the term "distal" means the portion of the device that is farthest from the physician and the term "proximal" means the portion of the device that is nearest to the physician.

FIG. 1 illustrates a device 10 for preparing foam in accordance with embodiments of the present invention. The device 10 includes a first housing 14, a second housing 16 and a valve 18. Preferably, the first housing 14, the second housing 16 and the valve 18 are nonremovably operably connected to prevent leaking during operation of the device due to improper connection of the housings to the valve. The device 10 further includes a handle 22 with the first housing 14 and the second housing 16 positioned at least partially within the handle 22. The valve 18 is operably connected to the first housing 14 and the second housing 16 and includes a control arm 26 for selectively positioning the valve 18 in relation to the first housing 14 and the second housing 16 as described in more detail below. The valve 18 may also include markings 20 or other indicators on a face 21 of the valve 18 to indicate the position of ports within the valve. The ports are discussed below with reference to FIGS. 3A-3D. A catheter 28 may be removably connected to the device 10 at a port 29 to deliver the foam to a patient. A vial 30 containing a liquid to mix with a gas to generate the foam may also be removably operably connected to the device 10. (See FIG. 3A.)

Figure 2:
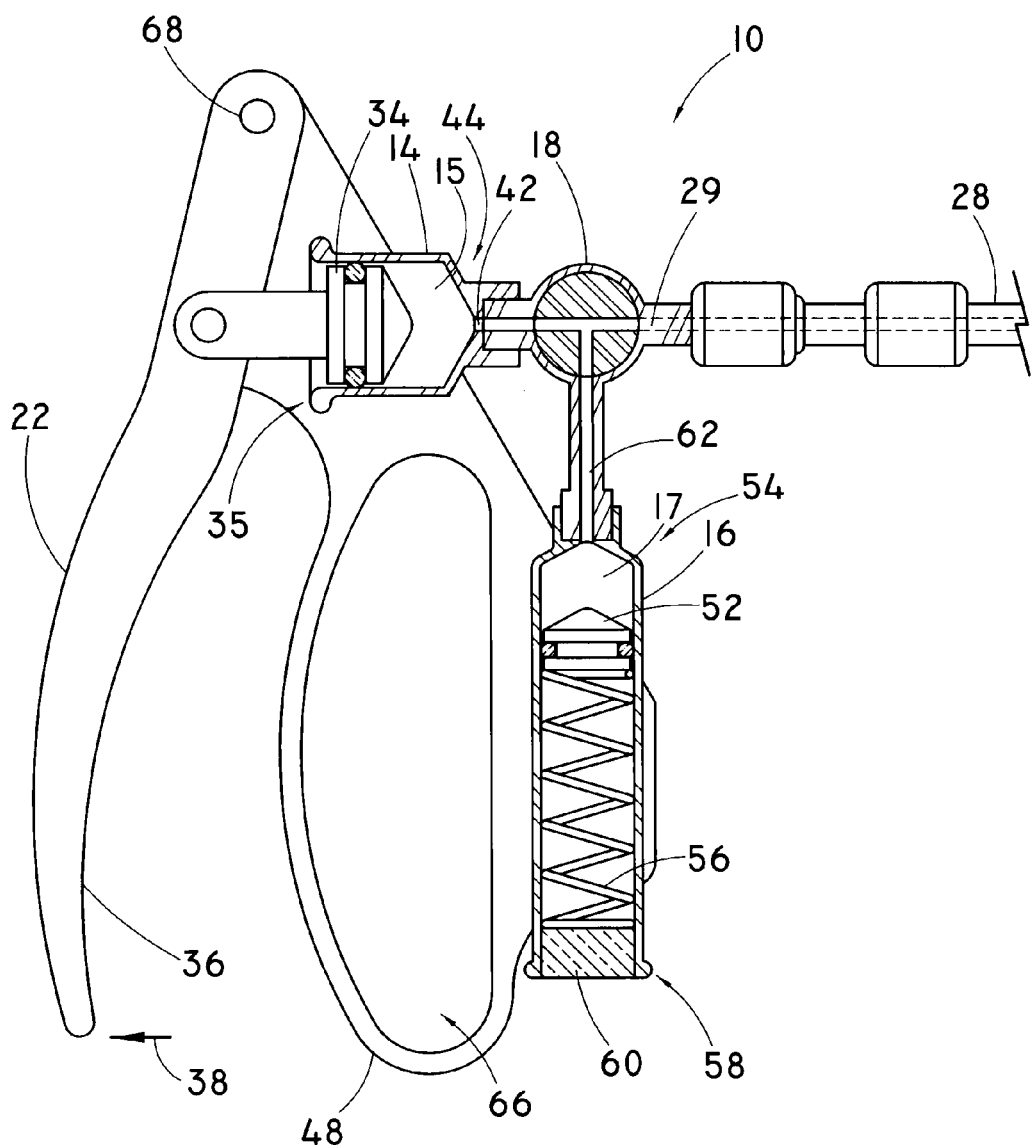
FIG. 2 is a sectional view of the device shown in FIG. 1.

FIG. 2 illustrates a sectional view of the device 10 shown in FIG. 1. As shown in FIG. 2, the first housing 14 may be positioned horizontally within a portion of the handle 22. The first housing 14 includes a first chamber 15 formed within the first housing 14. A movable member 34 is positioned at a second end portion 35 of the first housing 14 and is movable within the first housing 14. The movable member 34 is operably connected to a lever 36 of the handle 22. The first housing 14 includes an outlet 42 at a first end portion 44. The outlet 42 is operably connected to the valve 18.

As shown in FIG. 2, the device 10 includes the second housing 16 that may be positioned vertically within at least a portion of a gripping portion 48 of the handle 22. The second housing 16 includes a second chamber 17 formed within the second housing 16. A movable member 52 is positioned within the second housing 16. The movable member 52 is biased toward a first end portion 54 of the second housing 16 by a biasing member 56 positioned within the second housing 16. A second end 58 of the second housing 16 may be closed. The closed second end 58 provides a surface 60 against which the biasing member 56 abuts to bias the biasing member 56 toward the first end portion 54 of the housing 16. The first end portion 54 of the housing 16 also includes an outlet 62 operably connected to the valve 18. In some embodiments, the second housing 16 may be longer and narrower than the first housing 14. The shorter first housing 14 provides a shorter stroke to move the movable member 32 forward and thus causing less fatigue for the operator. By way of non-limiting example, the second housing 16 may be four times as long as the first housing. Other ratios are possible including ranges from 1:1 to 10:1 and more and are within the scope of the present invention. In some embodiments, the volume of the first chamber 15 and the second chamber 17 may be equal so that a shorter first housing may be wider than the longer and narrower second housing. The volumes of the first chamber 15 and the second chamber 17 may also be different. In some embodiments, the volume of the second chamber 17 is greater than the volume of the first chamber 15.

The handle 22 includes the lever 36 and the gripping portion 48 as shown in FIG. 2. The gripping portion 48 includes an opening 66 and is sized and shaped so that the operator can grasp the gripping portion 48 and manipulate the lever 36 with the same hand. The lever 36 is movable between a first extended position 38 shown in FIG. 2 and a second depressed position 40 shown in FIG. 3C. The lever 36 may be pivotally connected to an upper portion 68 of the handle 22 so that the operator may use a short stroke of the lever 36 to generate the foam as discussed in detail below.

Figure 3A:
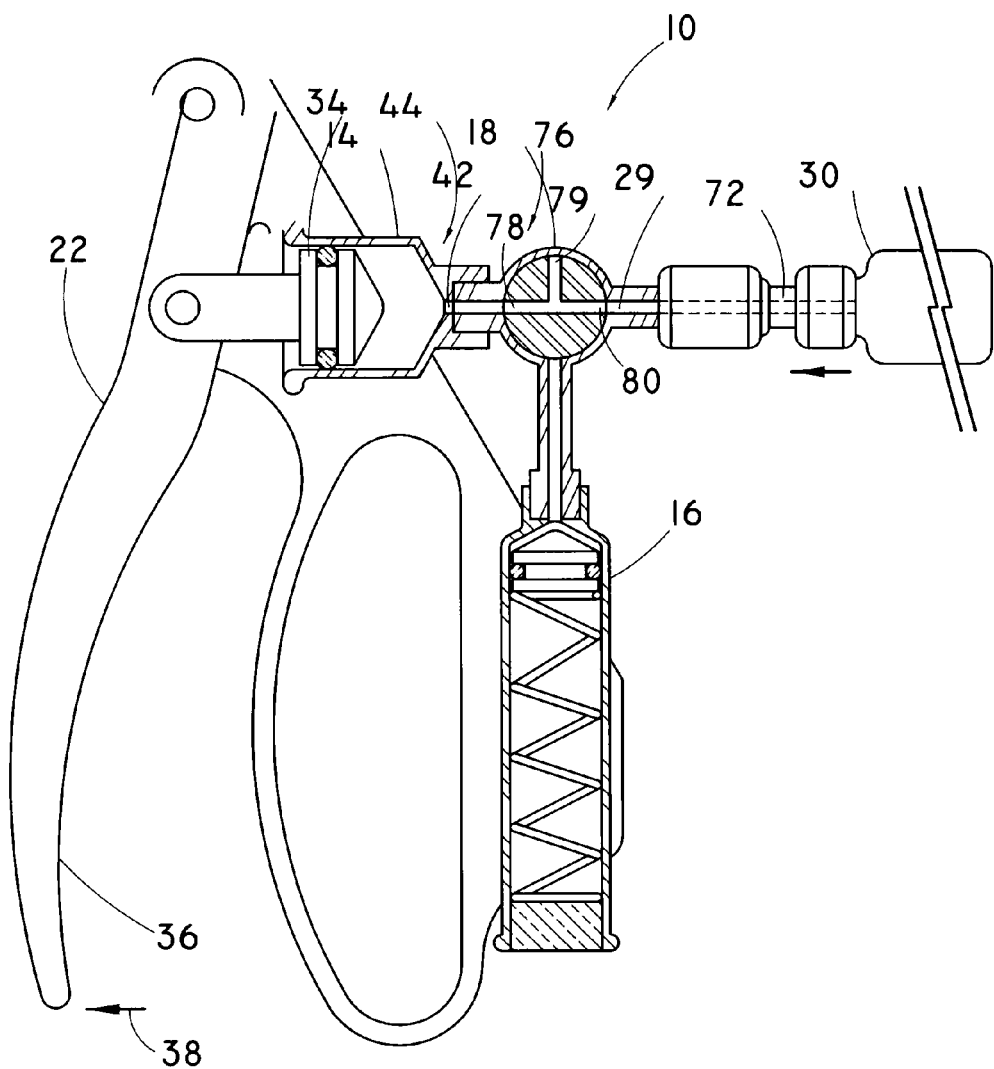
FIGS. 3A-3D are sectional views of the device shown in FIG. 1 showing different valve positions and handle configurations.

In some embodiments, the valve 18 may be a three-way valve to provide selective connection between the first chamber 15 and the second chamber 17 and the catheter 28 or the vial 30. The valve 18, as shown in FIG. 3A, includes three ports 78, 79, 80 that are rotatable within the valve 18 to operably connect with outlets 42, 62 and/or an opening. Additional valve configurations may also be used with the device 10, provided that the valve configuration can selectively connect the housing 14, the housing 16 and the catheter or vial in the configurations discussed below with reference to FIGS. 3A-3D.

The first housing 14 and the second housing 16 are preferably non-removably connected to the valve 18 to avoid the leakage problems that can arise with a removable connection between the housings 14, 16 and the valve 18. The non-removable connection may be formed using any type of connection known to one skilled in the art. By way of non-limiting example, the connection may be formed by gluing, welding, soldering, molding, and the like. The non-removable operable connection may also include tubing and the like included between the first housing 14 and the valve 18 and the second housing 16 and the valve 18. The device 10 may be provided to the operator as a sterile device and may be disposable.

Operation of the device 10 will be described below with reference to FIGS. 3A to 3D. As shown in FIG. 3A, the valve 18 is positioned in a first position 76 for loading a foamable liquid into the device 10. In the first position 76 of the valve 18, the port 78 operably connects to the outlet 42 of the first housing and to the port 29 of the device 10. The port 29 is operably connected to the vial 30 containing the foamable liquid. The vial 30 may be connected to the device 10 using a connector 72 provided on the device 10 so that the foamable liquid within the vial 30 can flow into the first chamber 15. In some embodiments, the connector 72 may be a Luer connector or other type of removable connection known in the art. The liquid may flow into the first chamber 15 by pulling the lever 36 of the handle 22 to draw the liquid from the vial 30 into the first chamber 15 or the contents may be forced out the vial 30 and into the first chamber 15. In some embodiments, the handle 22 may include a biasing member 57 to bias the lever 36 of the handle 22 to assist in drawing the liquid into the first chamber 15 (See FIG. 4). In other embodiments, the contents of the vial 30 may be withdrawn into a syringe and injected into the port 29 of the device 10 (not shown).

Figure 3B:
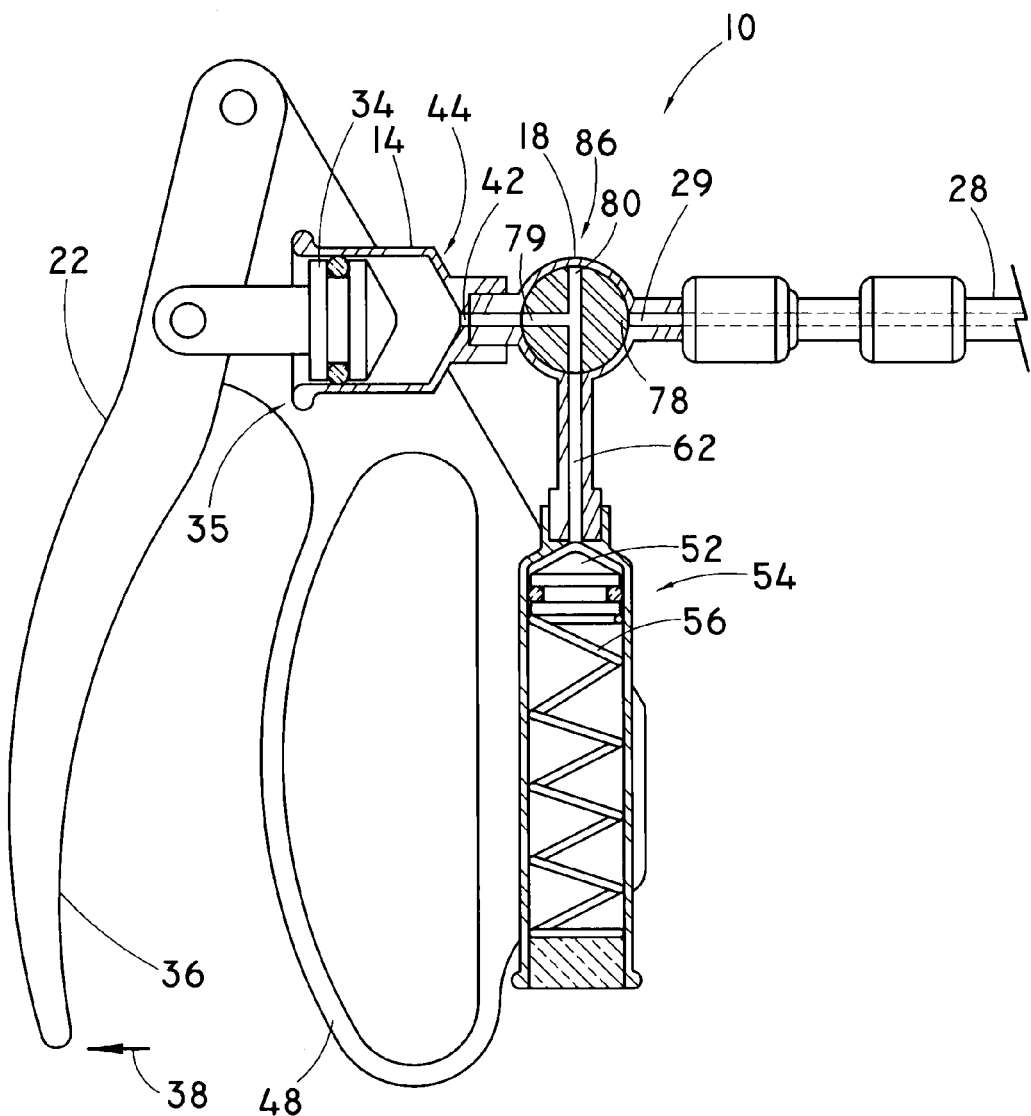

Once the liquid is loaded into the first chamber 15 of the first housing 14, the valve 18 is moved to a second position 86 as shown in FIG. 3B. The valve 18 is rotated 90° from the first position 76 to the second portion 86. In the second position 86, the port 79 is operably connected to the outlet 42 and the port 78 is operably connected to the outlet 62 of the second housing 16 and thus fluidly connecting the first chamber 15 with the second chamber 17. In the second position 86, the port 29 is closed. The vial 30 may be disconnected from the connector 72.

Figure 3C:
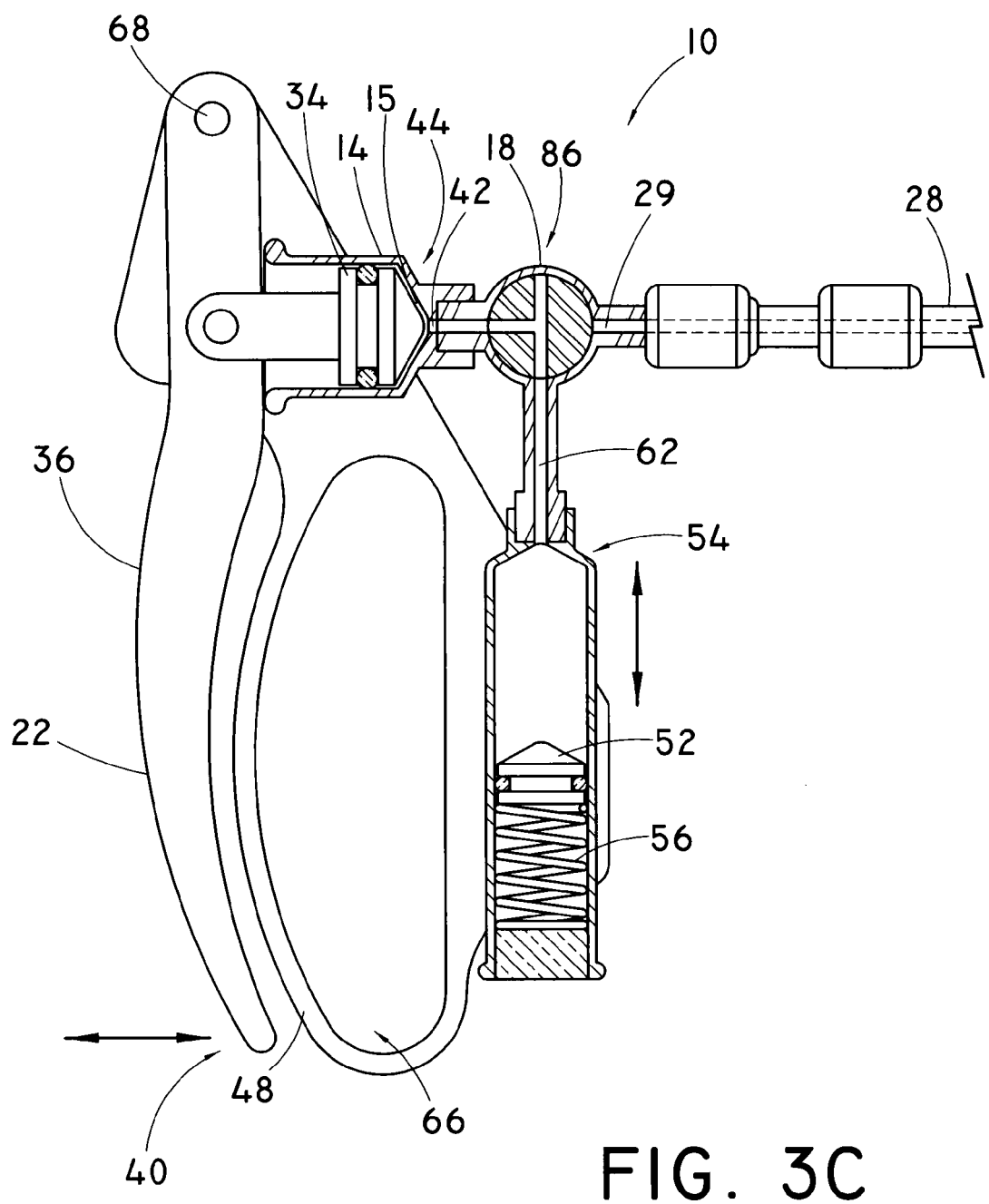

With the valve in the second position 86 so that the first chamber 15 and the second chamber 17 are fluidly connected, the handle 22 is manipulated by the operator using one hand to generate foam by mixing the liquid in the first chamber 15 with the gas in the second chamber 17 in a sealed system. The liquid and gas are rapidly forced back and forth between the first chamber 15 and the second chamber 17 to generate the foam. The lever 36 of the handle 22 moves between a first position 38 shown in FIG. 3B to a second position 40 shown in FIG. 3C. In operation, the lever 36 is pressed toward the gripping portion 48 of the handle 22 toward the second position 40 which moves the first movable member 34 toward the first end portion 44 of the first housing 14. The volume of the first chamber 15 is decreased and the liquid is forced out of the first chamber 15 through the port 79 into port 78 of the valve 18 and into the second chamber 17 of the second housing 16. The volume of the second chamber 17 is increased as shown in FIG. 3C.

The biasing member 56 in the second housing 16 then biases the second movable member 52 toward the first end portion 54 of the second housing 16 to decrease the volume of the second chamber 17. As the second moving member 52 is biased distally or upward toward the first end portion 54, the volume of the second chamber 17 is decreased and the liquid/gas mixture is forced back through the valve 18 and into the first chamber 15 as shown in FIG. 3B. The first movable member 34 is forced proximally to the second end portion 35 of the first housing 14 increasing the volume in the first chamber 15 and the lever 36 is returned to the first position 38. The operator only needs one hand to move the lever 36 of the handle 22 from the first position 38 to the second position 40 and the biasing member 56 of the second housing provides the force to return the lever 36 to the first position 38. The biasing member may be any type of biasing member known in the art having sufficient biasing force to overcome the hydrodynamic drag between the first chamber 15 and the second chamber 17 so that the lever 36 is returned to the first position 38. By way of non-limiting example, the biasing member may be a spring, an elastomer, a gas, a foam and the like.

The liquid is agitated with each cycle between the first and second chambers 15, 17 to generate the foam. The number of cycles between the first and second chambers 15, 17 will depend on several variables, including, but not limited to, the viscosity of the liquid, the type of liquid, the volume of liquid and gas, the size of the ports, and the like.

The catheter 28 may be connected to the connector 72 in preparation for delivery of the foam to a patient after the vial 30 is removed. The term "catheter" as used herein refers to any delivery device that may be used to transfer the foam from the device 10 to the patient.

Figure 3D:
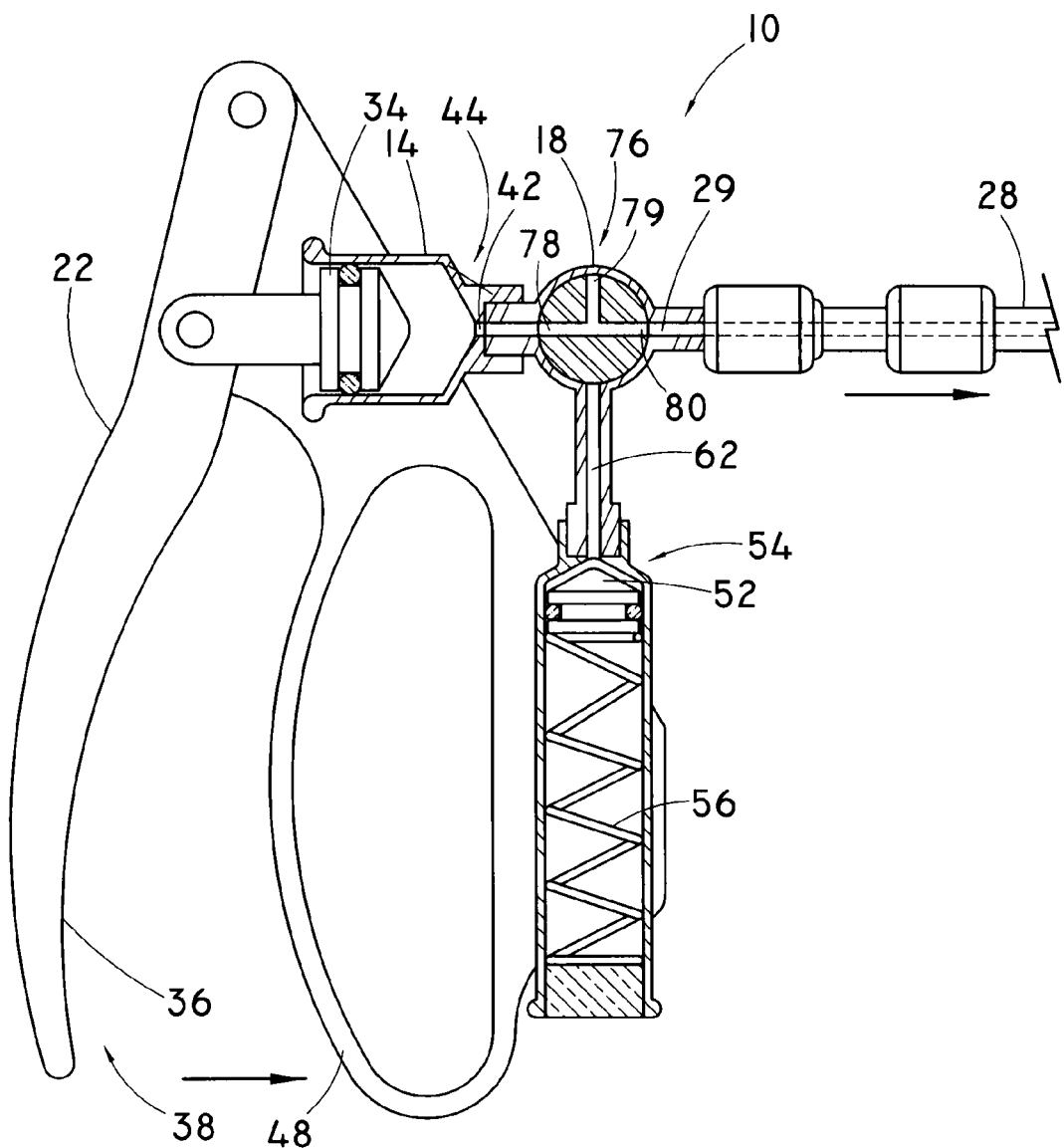

With the catheter 28 connected to the device 10, the foam is ready to be delivered to the patient. The foam is in the first chamber 15 and the lever 36 of the handle 22 is in the first position 38 and the movable member 32 of the first housing 14 is positioned in the second end portion 35. The biasing member 56 in the second housing 16 is biased toward the first end portion 54 and the volume of the second chamber 17 is diminished. The valve 18 is then returned to the first position 76 so that the port 78 is fluidly connected to the outlet 42 of the first housing 14 and the port 80 is fluidly connected to the port 29 and the catheter 28 as shown in FIG. 3D. The port 79 is closed.

With the valve 18 positioned in the first position 76 and the catheter 28 fluidly connected to the first chamber 14 having the foam therein, the foam is deliverable to a patient. The operator depresses the lever 36 of the handle 22 to distally advance the movable member 32 toward the first end portion 44 of the first housing 14 to force the foam through the valve 18 into the catheter 28 and into the patient. The operator may control the amount of foam delivered to the patient by controlling the forward movement of the lever 36. The valve 18 may be returned to the second position to close the fluid connection to the port 29 and the catheter 28.

Optionally, the operator may need to provide additional foam to the patient to complete the treatment. If enough time passed since the foam was generated, additional agitation cycles may be required to regenerate the foam. The foam may be regenerated from the mixture remaining in the first housing 14 without needing to reconnect anything to the device 10. With the valve 18 in the second position 86 shown in FIG. 3B, using the same procedure described above, the foam can be regenerated by depressing the lever 36 of the handle 22 from the first position 38 to the second position 40. The biasing member 56 biases the second movable member 52 toward the first end portion 54 of the second chamber 17 forcing the foam through the valve 18 and into the first chamber 15. The first movable member 32 is biased back to the second end portion 35 and moves the lever 36 back to the first position 38. The foam generating movement of the handle 22 may be repeated as many times as needed to generate a sufficiently viscous foam for injection into the patient.

When the foam is ready, the valve 18 is returned to the first portion 76 shown in FIG. 3D and additional foam is delivered to the patient.

Figure 4:
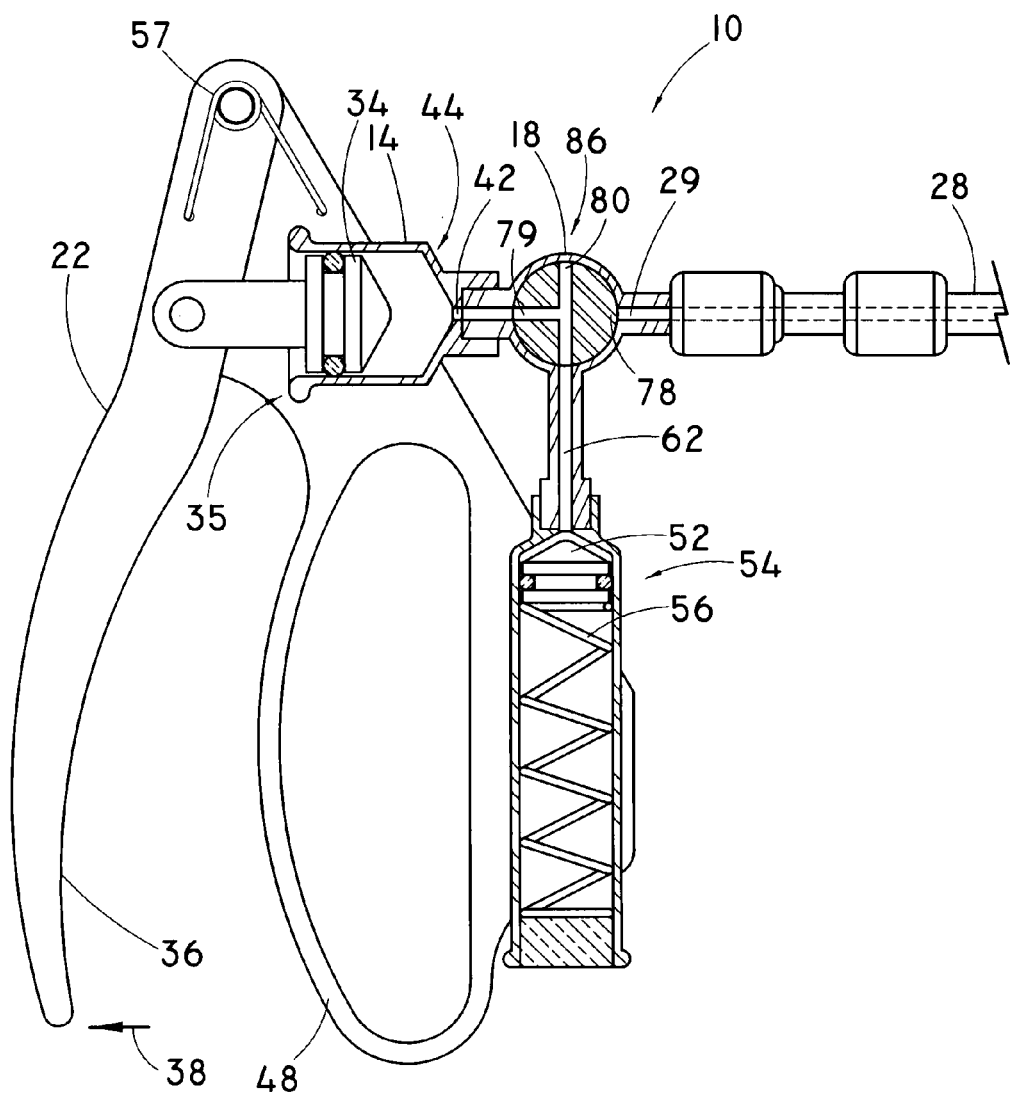
FIG. 4 is a sectional view of an alternative embodiment of the present invention.

In some embodiments, as shown in FIG. 4, the handle 22 may also include a biasing member 57 to cooperate with the biasing member 56 in the second housing 16 to bias the lever 36 of the handle 22 to the first position 38. By way of non-limiting example, the handle biasing member 57 may be provided as a spring, such as a leaf spring or coil spring.

In some embodiments, the liquid used to generate the foam may be a sclerosing agent. By way of non-limiting example, the sclerosing agent may be sodium tetradecyl sulfate (STS). The STS may be used in concentrations known in the art for sclerosing varicose veins, for example 0.25-0.4% for reticular veins (2-4 mm) and venulectasias (1-2 mm) and 0.1-0.2% for telangiectasias (<1 mm).

In some embodiments, the sclerosing agent may be mixed with a gas such as air or $CO_2$. Other concentrations and other sclerosing agents and gasses are possible and the examples given above are merely for example.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of a sclerosing agent for illustrative purposes only. Application of the principles of the invention to any other foamable liquid, by way of non-limiting examples, are within the ordinary skill in the art and are intended to be encompassed within the scope of the attached claims.

The invention claimed is:

1. A device for preparing foam; the device comprising:
    a first housing having a first chamber therein and a first movable member positioned at least partially within the first housing;
    a second housing having a second chamber therein, the second chamber being selectively and operably connectable to the first chamber, the second housing comprising a biasing member and a second movable member therein, the biasing member biasing the second movable member toward a first end portion of the second housing;
    a valve operably connected to the first chamber and the second chamber and movably positionable to selectively control the connection between the first chamber and the second chamber; and
    a handle operably connected to the first movable member, the handle comprising a first portion and a second portion movable relative to each other, the handle being movable to bias the first movable member toward a first end portion of the first housing,
    wherein the handle and the biasing member cooperatively bias the first movable member and the second movable member so that the first movable member is biased toward a first end portion of the first housing and the second movable member is biased toward a second end portion of the second housing as the handle biases the first movable member toward the first end portion of the first housing.

2. The device of claim 1, wherein the first housing and the second housing are nonremovably operably connected to the valve.

3. The device of claim 1, wherein the second housing comprises a closed second end.

4. The device of claim 1, wherein the device further comprises an outlet.

5. The device of claim 4, wherein the outlet is removably connectable to a vial, the vial providing a foamable liquid or is removably connectable to a catheter for delivering foam to a patient.

6. The device of claim 1, wherein the first housing has a shorter length than the second housing.

7. The device of claim 1, wherein the handle further comprises a handle biasing member for biasing the handle to an open position.

8. The device of claim 1, wherein the second chamber has a volume equal to or greater than a volume of the first chamber.

9. The device of claim 1, wherein the first housing is positioned at least partially within a portion of the handle and substantially perpendicular to a lever of the handle.

10. The device of claim 1, wherein the second housing is positioned at least partially within a portion of the handle and substantially parallel to a lever of the handle.

11. A method of preparing and delivering foam, the method comprising:
    providing a device for preparing foam, the device comprising:
        a first housing having a first chamber therein and a first movable member positioned at least partially within the first housing;
        a second housing having a second chamber therein, the second chamber being selectively and operably connectable to the first chamber, the second housing comprising a biasing member and a second movable member therein, the biasing member biasing the second movable member toward a first end portion of the second housing;
        a valve operably connected to the first chamber and the second chamber and movably positionable to selectively control the connection between the first chamber and the second chamber; and
        a handle operably connected to the first movable member, the handle comprising a first portion and a second portion;
    depressing the first portion of the handle to move the first portion of the handle relative to the second portion of the handle from a first position to a second position and biasing the first movable member toward a first end portion of the first housing to force a liquid out of the first chamber and into the second chamber and compressing the biasing member toward a second end portion of the second housing as the liquid is forced into the second chamber;
    expanding the biasing member toward the first end portion of the second housing to move the second movable member toward the first end portion of the second housing to force the liquid from the second chamber into the first chamber and moving the first movable member and handle back to the first position.

12. The method of claim 11, further comprising selectively positioning the valve in a first position connecting the first housing to an outlet, the outlet connected to a vial having a foamable liquid therein and delivering the liquid to the first chamber.

13. The method of claim 11, further comprising selectively positioning the valve in a second position connecting the first housing to the second housing to transfer the liquid between the first chamber and the second chamber and foaming the liquid.

14. The method of claim 13, further comprising forcing the liquid between the first chamber and the second chamber greater than one transfer between the first chamber and the second chamber and generating foam.

15. The method of claim 11, further comprising selectively moving the valve from the second position to a first position connecting the first chamber to an outlet having a catheter connected thereto and delivering the foam to a patient.

16. The method of claim 15, further comprising repositioning the valve in the second position and refoaming the liquid remaining in the first chamber.

17. The method of claim 11, comprising providing a sclerosing liquid to the first chamber.

18. The method of claim 11, comprising providing a gas in the second chamber for mixing with the liquid.

19. The method of claim 11, providing the first housing and the second housing nonremovably operably connected to the valve.

* * * * *